United States Patent
Pavlu et al.

(10) Patent No.: US 7,070,071 B2
(45) Date of Patent: Jul. 4, 2006

(54) DISPENSING APPARATUS AND METHOD FOR LIQUID PRODUCTS, PARTICULARLY MEDICINAL PRODUCTS

(75) Inventors: Bohdan Pavlu, Nacka (SE); Hans Himbert, Bromma (SE); Christian Péclat, Neuchatel (CH); Emmanuel Gremion, Echarlens (CH); Daniel Siegfried, Bern (CH); Alain Saurer, Neuchâtel (CH); Joel Fontannaz, Liebefeld (CH)

(73) Assignee: Agouron Pharmaceuticals, Inc., La Jolla, CA (US)

( * ) Notice: Subject to any disclaimer, the term of this patent is extended or adjusted under 35 U.S.C. 154(b) by 216 days.

(21) Appl. No.: 10/657,594

(22) Filed: Sep. 8, 2003

(65) Prior Publication Data

US 2005/0077315 A1    Apr. 14, 2005

Related U.S. Application Data

(60) Provisional application No. 60/415,015, filed on Oct. 1, 2002.

(30) Foreign Application Priority Data

Sep. 23, 2002    (SE)    .................................... 0202800

(51) Int. Cl.
    *B65D 88/54*    (2006.01)
(52) U.S. Cl. ....................... 222/325; 222/401; 604/295
(58) Field of Classification Search ............. 222/321.7, 222/321.8, 324–325, 181.1, 105, 181.2, 420–422, 222/321.6, 185.1, 182–183, 401; 604/133–134, 604/294–302
    See application file for complete search history.

(56) References Cited

U.S. PATENT DOCUMENTS

| 4,623,337 | A |   | 11/1986 | Maurice |
| 5,190,191 | A |   | 3/1993 | Reyman |
| 5,607,410 | A | * | 3/1997 | Branch ....................... 604/302 |

(Continued)

FOREIGN PATENT DOCUMENTS

DE    19948462    9/2000

(Continued)

*Primary Examiner*—Frederick C. Nicolas
(74) *Attorney, Agent, or Firm*—Edward D. Robinson; Bryan C. Zielinski

(57) ABSTRACT

A dispensing apparatus for a liquid product, the apparatus comprising a) a housing (2) or frame (3), b) a receptacle (4) for the liquid with a feed nozzle (4a) arranged substantially stationary with respect to the housing or frame, c) a dosing chamber (11) having an orifice (11a), d) a mechanism arranged to allow at least ejection of liquid through the orifice and e) a through passage (7) arranged to allow the ejected liquid to pass in a direction different from the feed nozzle or opening. The mechanism comprises a mobile element arranged movable with respect to the housing or frame between at least a first position in which the orifice of the dosing chamber and the feed nozzle or opening are in flow communication and a second position in which the orifice and the through passage are in flow communication and the mechanism is arranged to allow aspiration of liquid through the orifice when the mobile element is in the first position and ejection of liquid through the orifice when the mobile element is in the second position. A method for operating the device comprises the steps of i) connecting the orifice and the nozzle or opening in flow communication, ii) filling liquid into the dosing chamber through the orifice, iii) aligning the orifice with the through passage, and iv) ejecting liquid from the dosing chamber through the orifice.

56 Claims, 12 Drawing Sheets

U.S. PATENT DOCUMENTS

| | | | |
|---|---|---|---|
| 5,665,071 A * | 9/1997 | Wyrick | 604/134 |
| 5,836,911 A | 11/1998 | Marzynski et al. | |
| 5,944,702 A | 8/1999 | Py | |
| 6,398,766 B1 * | 6/2002 | Branch | 604/302 |
| 6,758,837 B1 * | 7/2004 | Peclat et al. | 604/295 |
| 6,814,265 B1 * | 11/2004 | Clifford et al. | 222/420 |

FOREIGN PATENT DOCUMENTS

| | | |
|---|---|---|
| EP | 0823246 | 2/1998 |
| FR | 2647757 | 12/1990 |
| WO | WO90 13497 | 11/1990 |
| WO | WO92 20455 | 11/1992 |

* cited by examiner

DISPENSING APPARATUS AND METHOD FOR LIQUID PRODUCTS, PARTICULARLY MEDICINAL PRODUCTS

RELATED APPLICATION

The present application claims priority under 35 U.S.C. §119 of U.S. application Ser. No. 60/415,015 filed Oct. 1, 2002.

FIELD OF THE INVENTION

The present invention concerns a dispensing apparatus for liquid products, particularly medicinal products, such as an ophthalmic solution.

BACKGROUND OF THE INVENTION

Although the principles of the present invention may have utility in many areas, for convenience it will be described mainly in connection with liquid treatment of eyes. Typically the medical preparation has to be delivered in a fairly well defined volume to assure a specified dose to be delivered or absorbed. A large surplus cannot be allowed due to improper systemic physiological effects from absorbency in non-target tissues or drainage of excess amounts through the tear channel into the throat cavity or the inconveniences caused by overflow on face and clothes. Also price considerations apply for expensive medications. As an example, the treatment of glaucoma requires frequent daily administrations of e.g. prostaglandins, beta-blockers or other expensive active ingredients, all having other then the desired pressure relieving action when absorbed by other body tissues than the eye. Small volume dosing is negatively affected by even small uncontrolled or dead spaces in delivery equipments used. Moreover, medical preparation components may be sensitive to degradation or absorption at prolonged exposure to materials and extended surfaces present in delivery devices. Similar considerations apply for sterility preservation. With regard to stream quality, proper administration of small amounts is complicated by the fact that the active ingredients cannot enter the eye but through the limited area of the cornea. It is also necessary that the entire dose can be delivered before the triggered blink reflex closes the eyelid.

A large number of devices are already known for applying a determined quantity of a liquid medicinal product onto a part of the body, such as an ophthalmic solution on the surface of the eye. These devices generally rely on the principle of a syringe which can be either pre-filled with a determined quantity of liquid, or graduated to suck up said quantity of liquid contained in a separate bottle, or connected to a fixed receptacle in permanent communication with the dosing chamber of the syringe, as is described for example in one of the embodiments of U.S. Pat. No. 4,623,337. It will be observed that permanently feeding the dosing chamber from the receptacle via gravity means that neither the precision of the quantity of liquid to be ejected, nor the sterility thereof can be guaranteed. In these devices, the pressure exerted on the plunger, manually or automatically, is generally exerted in the same direction as that of the liquid jet, as is described for example in International Patent Application No. WO 92/20455.

The direction of the jet can sometimes be deviated by bent conduits, but it is then difficult to control the force with which the jet reaches its target. A device of this kind is like, for example, that disclosed in French Patent No. FR 2 647 757 for food products or cosmetics in liquid or paste-like form, for which respecting a given ejection pressure is of no importance.

In the case of a an ophthalmic solution, it is, however, very important not only to control very precisely the dose to be ejected for obvious reasons of safety and efficacy of the treatment, but also in order to be able to control the impact pressure of the liquid jet on the eye, which certain devices attempt to achieve by using an eyepiece or a spacing member applied to the periphery of the target to impose a fixed distance with respect to the liquid ejection orifice, as is disclosed for example in U.S. Pat. Nos. 4,623,337 and 5,836,911. It will be observed however that these devices do not always allow the impact force of the liquid jet to be reproduced when the pressure is exerted directly on the plunger manually.

Thus, the dispensing apparatuses of the prior art provide individual solutions to particular problems, but none of them allows all of the aforementioned problems to be simultaneously resolved.

SUMMARY OF THE INVENTION

The object of the present invention is thus to provide a dispensing method and device capable of avoiding the problems discussed above. More particularly an object is to provide a method and device system capable of ejecting, e.g. with a new design of the plunger head leaving practically no ullage, a precise dose of liquid, such as an ophthalmic solution, with an adjustable impact pressure on the target and the dose and impact pressure being independent of the way in which the pressure is exerted on the actuator. The apparatus according to the invention includes a mechanism allowing sterility conditions to be improved, given that the receptacle is only in communication with the dosing chamber except for a brief moment during ejection when it is placed in communication with the external environment for a few tenths of a second, during which time the pressure equilibrium is achieved by replacing the sucked up liquid with air. In addition the system allows uncontrolled and a dead spaces to be kept to a minimum. The apparatus is further very easy to use in particular for an ophthalmic solution.

These and other objects are reached by the characteristics set forth in the appended patent claims.

The movement of the actuator is preferably substantially perpendicular to the direction of ejection of the liquid, such that the pressure exerted on the actuator cannot modify the distance with respect to the target, for example the eye in the case of an dispensing ophthalmic solution.

According to a first embodiment, the mobile element is formed by a drum provided, on its flanks, with studs rotatably mounted in the two shells of the housing, and housing in its diametral part an assembly formed by the dosing chamber, the plunger and the return spring.

At the start of pressure on the actuator, the drum occupies a first filling position in which the orifice of the dosing chamber is opposite the receptacle feed nozzle. By continuing to press on the actuator, the drum rotates through an angle α to occupy a second ejection position in which the orifice of the dosing chamber is opposite the through passage of the housing.

In a second embodiment, the dosing chamber is formed in a unit secured to the frame, and the mobile element is formed by a mobile valve, held in the rest position by a return spring. At the start of pressure on the actuator, the valve occupies a first position for filling the dosing chamber through a channel formed in the thickness of said valve placing the orifice of the dosing chamber in communication with the receptacle nozzle. By continuing to press on the actuator the valve is brought into a second ejection position in which the orifice of the dosing chamber is placed in communication with the exterior through a hole of the valve located opposite the through passage of the frame.

In both embodiments, the actuator is returned to the rest position by resilient return means, wound by the travel of the plunger during the filling and ejection phases. In these two embodiments, in order to further increase the conditions of sterility, the actuator can include a panel blocking the through passage of the housing or frame from the exterior in the rest position, said panel including an orifice brought to face said through passage in the ejection position.

BRIEF DESCRIPTION OF THE DRAWING

Other features and advantages of the present invention will appear more clearly upon reading embodiment examples, given purely by way of non-limiting illustration, with reference to the annexed drawings, in which:

FIG. 3A shows an enlarged diagram of the pinion and pins shown in the exploded perspective view of FIG. 3;

FIGS. 5A to 9A show the different positions of the drive members in the phases corresponding to FIGS. 5 to 9;

DETAILED DESCRIPTION

Figure 1:
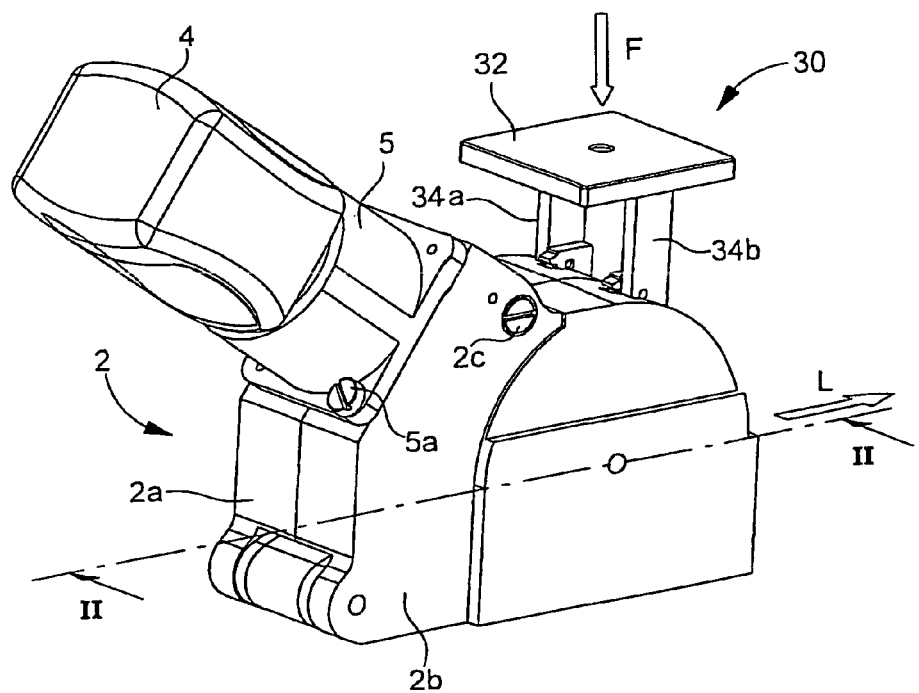
FIG. 1 shows a perspective view of a dispensing apparatus according to the invention without the external cover.
Figure 10:
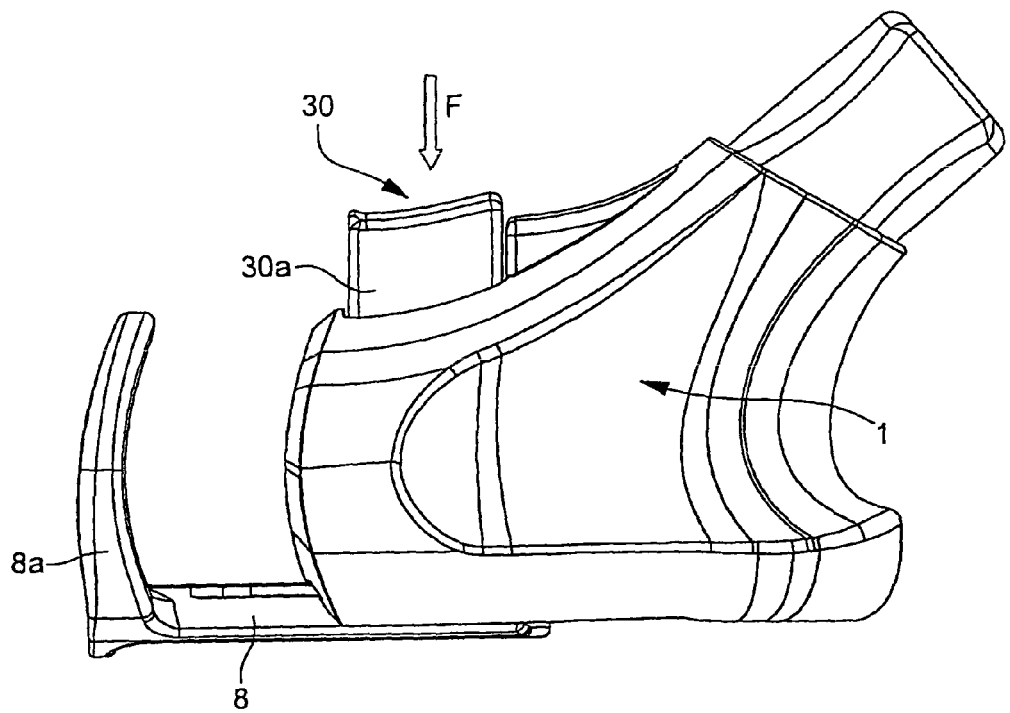
FIG. 10 shows a side view of a second embodiment of the invention.

In FIG. 1, FIGS. 1 and 10 show, in perspective, two embodiment examples of a dispensing apparatus according to the invention. In FIG. 1, the apparatus includes an external cover 1 marking the mechanism of a second embodiment which will be described hereinafter where the external cover has been removed, one can see that externally the apparatus includes a housing 2 formed of two shells 2a, 2b assembled by a screw 2c after positioning the contact surfaces by means of pins 2d visible in the exploded view of FIG. 3, to which reference will also be made in the description hereinafter. The liquid, which will have to be ejected from the apparatus in the direction of double arrow L, is contained in a receptacle 4 which, in this example, is a bottle ending in a feed nozzle 4a. Bottle 4 is secured to the apparatus by means of an adjustable clamp 5, to shells 2a, 2b by means of screws 5a. In FIG. 1, it can also be seen that actuator 30, the actuation of which by a force F is effected in a substantially perpendicular direction to the direction of ejection of the liquid. In this embodiment, the actuator take the form of a push button and is generally U-shaped with a head 32 extended by two branches 34a, 34b, the construction and functions of which will be described hereinafter.

Figure 4:
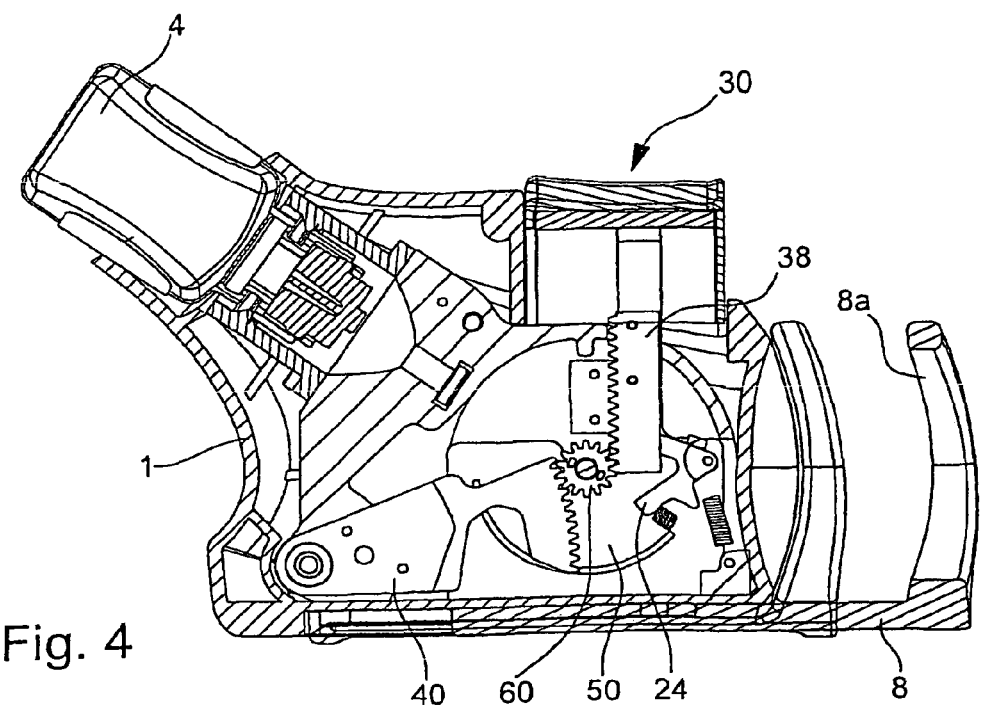
FIG. 4 shows a side view of the apparatus of FIG. 1 in which one shell of the housing and the drum have been removed.

Reference will also now be made to FIG. 4, in which external cover 1 has been kept, but shell 2b and drum 50 have been removed. Drum 50 forms, with the parts which drive it in one direction or another, the main mobile element of the mechanism according to the invention. Drum 50 includes on each of its flanks 52a, 52b studs 54a, 54b rotatably mounted in bearings 44a, 44b provided in the inner faces of shells 2a, 2b. Drum 50 also includes at its periphery an opening 56 corresponding to a through passage in which dosing chamber 11 will be mounted, provided with an ejection orifice 11a, a plunger 10 comprising a head 12, and a rod 13 having a groove 13a at its end. The particular structure of head 12, which contributes to the precision of the quantity of liquid ejected and to the non-contamination of the chamber by external polluting agents will be explained in more detail with reference to the second embodiment.

The drum also includes a slit 58 in which two lateral arms 22a, 22b of a staple 20 are engaged, said staple being snapped into groove 13a of rod 13, by compressing a spring 14 mounted on rod 13 of plunger 10, when said staple 20 is moved, from the bottom of slit 58 to the edge of drum 50. The movement of staple 20 is achieved by a double lever 24, articulated in its median part in shells 2a, 2b, each lever including an arm 26a pressing on each lateral arm 22a, 22b of staple 20. Each arm 26a of double lever 24 also includes a snug 28, allowing a safety catch 62 to be manoeuvred.

In proximity to slit 58, drum 50 also includes a notch 64 in which safety catch 62 will be engaged, the function of said catch being described hereinafter within the scope of the description of the working of the apparatus. Finally, drum 50 includes on each of its flanks 52a, 52b, two bean-shaped holes 66a, 66b, the function of which is explained hereinafter.

On each of studs 54a, 54b of drum 50 there is mounted a pinion 60, each pinion including along its axis two pins 61a, 61b, more clearly visible in enlarged FIG. 3A. When a pinion 60 is mounted on a stud 54a, 54b of the drum, pins 61a, 61b are engaged in holes 66a, 66b, such that, when pinion 60 is driven in rotation, it has a small angle of shake during which drum 50 is not driven in rotation.

In FIG. 4, it can be seen that pinions 60 mesh with the toothings, on the one hand, of actuator 30, and of a return member 40 on the other hand.

As indicated at the beginning, the actuator includes symmetrical branches 34a, 34b, the spacing of which substantially corresponds to the width of the drum. Each branch 34a, 34b is formed of an external part ending in a stop member 36, for manoeuvring arms 26b of lever 24, and of an internal part formed by a straight rack 38 extending on either side of stop member 36 in the longitudinal direction of branches 34a, 34b.

Return member 40 is formed by a double pivoting rack including two branches 40a, 40b connected by a bridge 42, the pivoting rack being articulated in shells 2a, 2b of housing 2. A return spring 46 allows the double rack to be kept in the low position when there is no pressure exerted on actuator 30 and to return it to this position when the actuator is released after having exerted pressure on the latter.

Finally, it can be seen that the inner surfaces of shells 2a, 2b each include a cam 6 having the shape of an arcuate rib. The end 22a, 22b of the lateral arms of staple 20 are capable of sliding on the external contour of rib 6 in order to keep spring 14 compressed during the rotation of drum 50 between the filling position and the ejection position. In the example illustrated cam 6 extends over an angle of approximately 120°.

Figure 2:
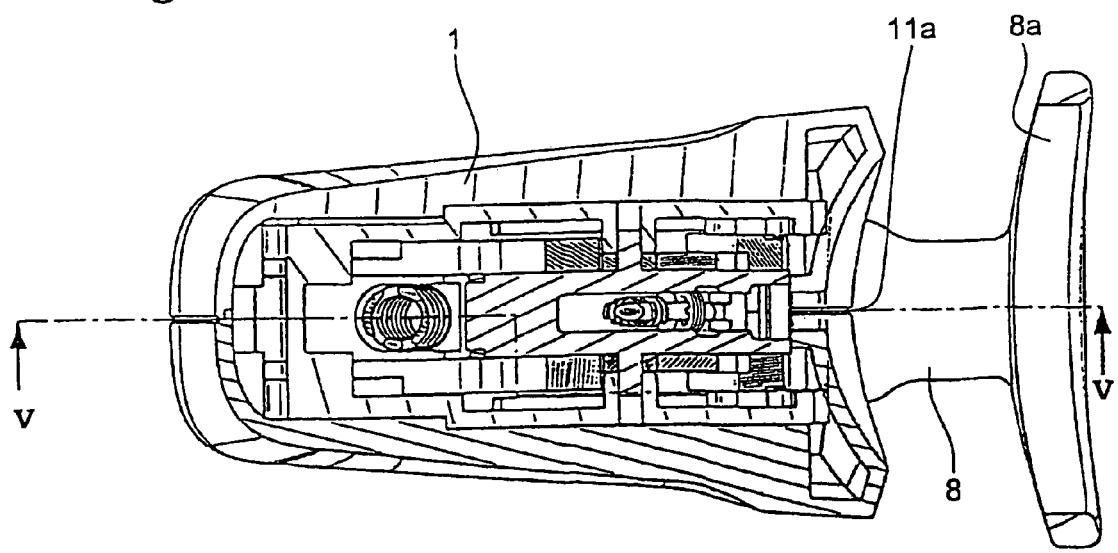
FIG. 2 shows a cross-section of the apparatus of FIG. 1, along the arrows II—II parallel to the base of the apparatus.
Figure 3:
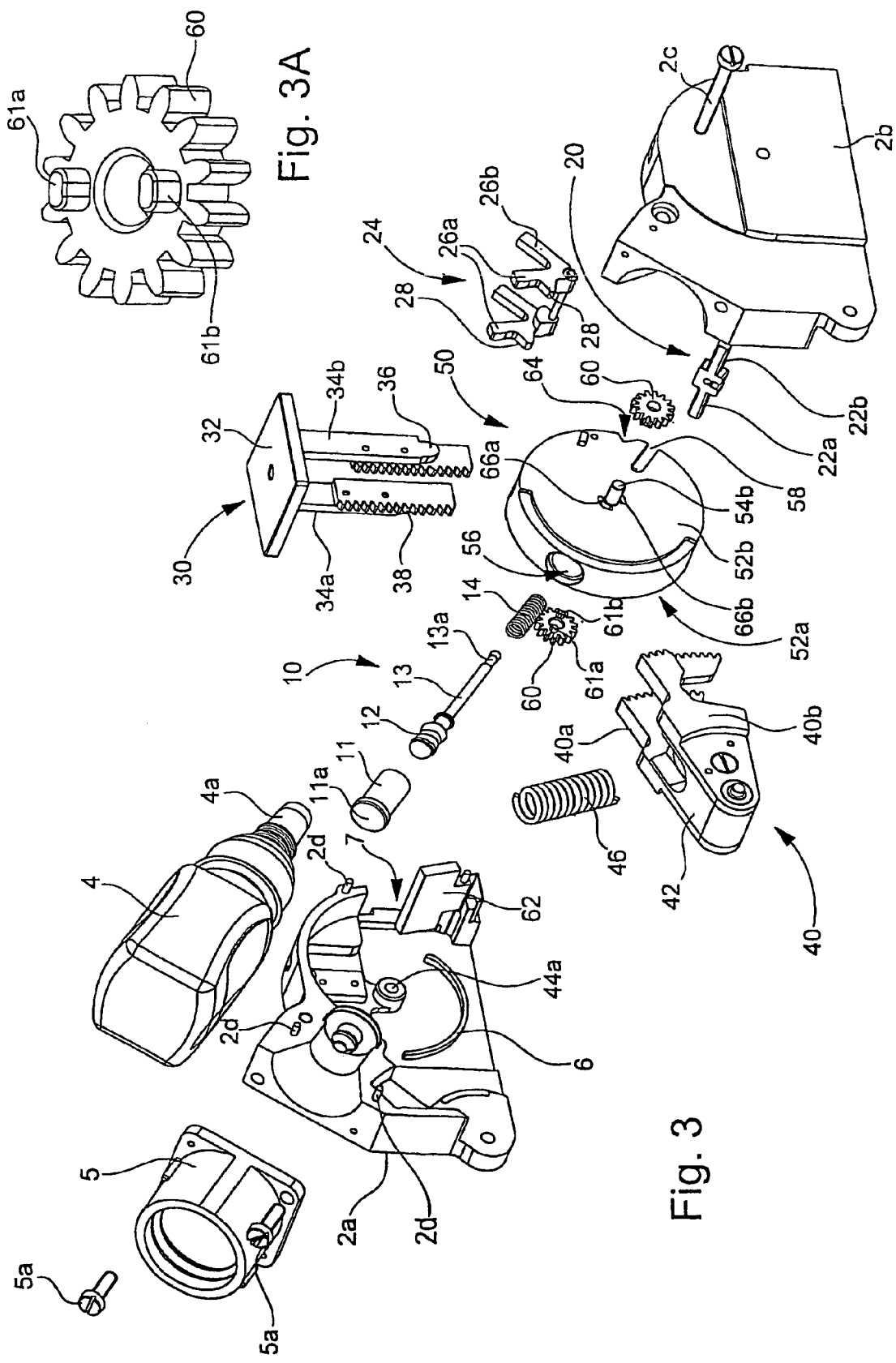
FIG. 3 shows an exploded perspective view of the apparatus of FIG. 1.

The parts which have just been described, essentially with reference to the exploded view of FIG. 3, appear at least partially in the cross-section of FIG. 2 where the mechanism is shown with its external cover 1 and a sliding member 8 for adjusting the distance between the ejection orifice and an eyepiece 8a located at its end. Sliding member 8 and eyepiece 8a are shown in two end positions in FIG. 4. FIG. 3 also shows the cross-section line V—V corresponding to FIGS. 5 to 9 which will now enable the operation of the mechanism to be explained.

The operation of this first embodiment is now described with reference to FIGS. 5 to 9.

Figure 5:
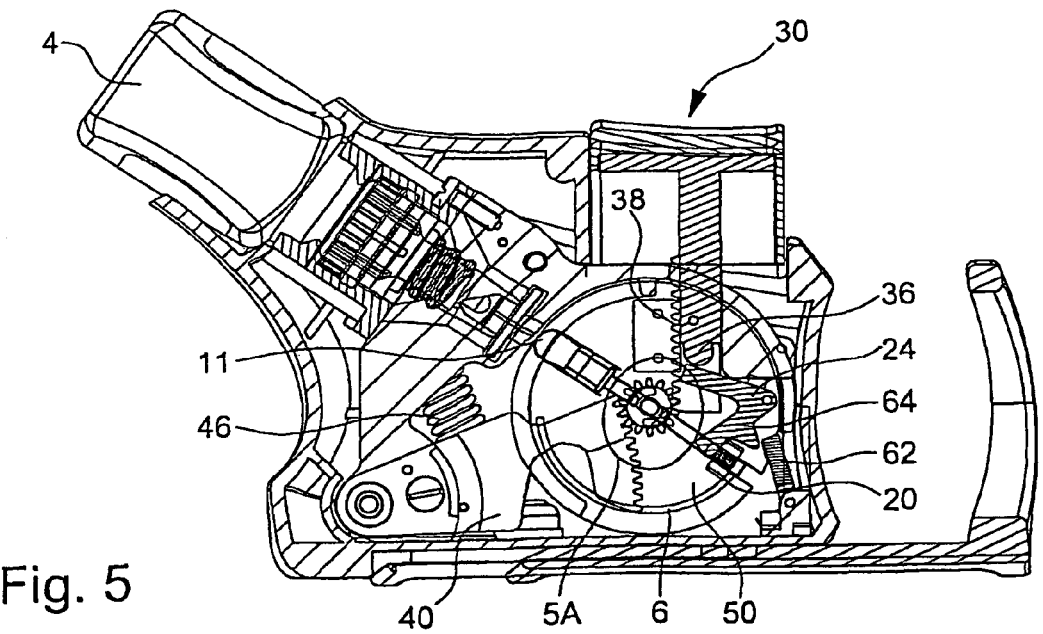
FIG. 5 shows a cross-section along the line V—V of FIG. 2, of the mechanism assembly in the rest position.
Figure 5A:
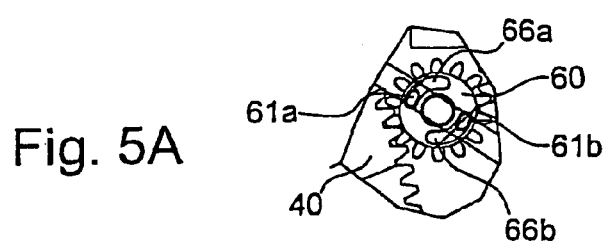

Rest Position (FIGS. 5 and 5A)

No pressure is exerted on actuator 30. Safety catch 62 is engaged in notch 64 of drum 50 and the orifice of dosing chamber 11 is opposite the nozzle of receptacle 4. Spring 46 rests on return rack 40, keeping pins 61a, 61b in the low position in holes 66a, 66b. The two ends of lever 24 are abutting respectively against stop member 36 and staple 20. As the plunger head is pressed against the bottom of the dosing chamber, receptacle 4 is perfectly insulated from the external environment, and leaves no ullage.

Figure 6:
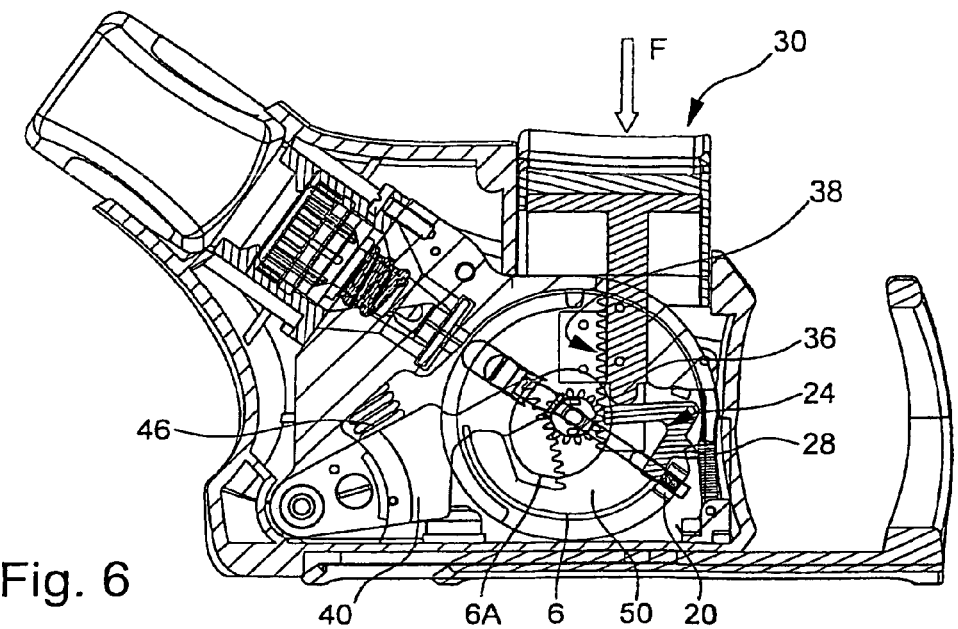
FIG. 6 corresponds to the suction phase of a determined quantity of liquid to be ejected.
Figure 6A:
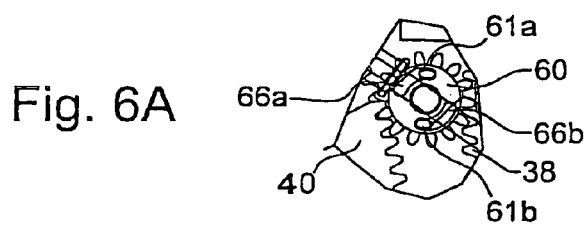
FIG. 6A shows an enlarged diagram of the pinion and return rack shown in the liquid suction phase of FIG. 6.

Dosing Chamber Filling Position (FIGS. 6 and 6A)

By exerting a pressure F on actuator 30, stop member 36 tips lever 24, and rack 38 drives pinion 60 to a high position in which pins 61a, 61b do not drive drum 50. In this step lever 24 pulls plunger 10 thus sucking up the liquid from bottle 4 to fill the dosing chamber to a position where staple 20 is placed behind cam 6. At this moment snug 28 of lever 24 pushes back safety catch 62 releasing drum 50. In this phase, spring 46 starts to be compressed.

Figure 7:
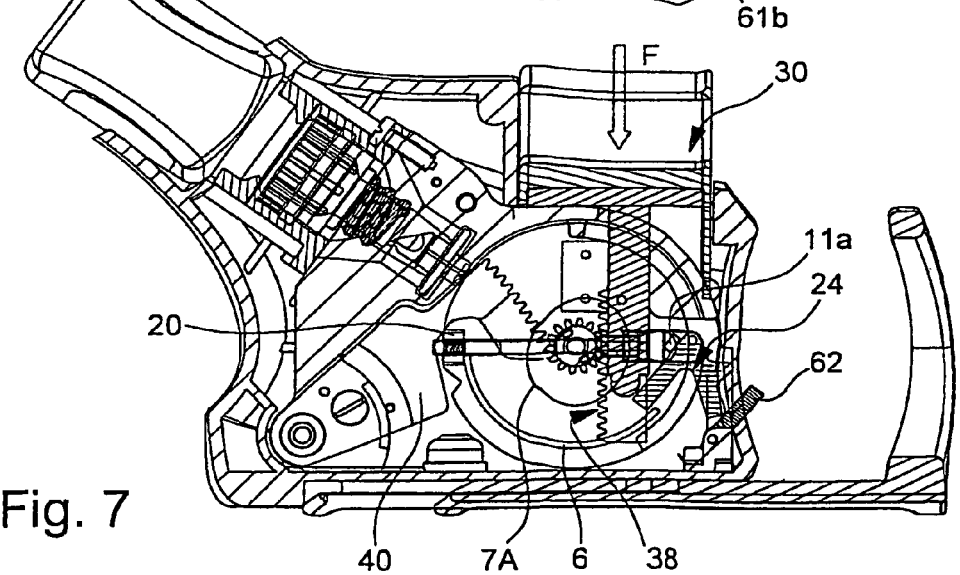
FIG. 7 corresponds to the rotation of the drum to the ejection position.
Figure 7A:
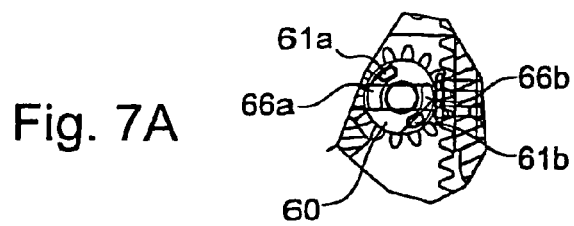
FIG. 7A shows an enlarged diagram of the pinion, pins and holes shown in the drum of FIG. 7.

Passage into the Ejection Position (FIGS. 7 and 7A)

By continuing to exert pressure F on actuator 30, rack 38 drives pinion 60 which itself rotates drum 50, by means of pins 61a, 61b which rest on one end of holes 66a, 66b. During this rotation, staple 20 follows via its lateral arms the external contour of the rib forming cam 6. FIG. 7 shows the position just preceding ejection, orifice 11a of dosing chamber 11 being substantially on the axis of ejection. Rack 40 then exerts maximum compression on spring 46.

Figure 8:
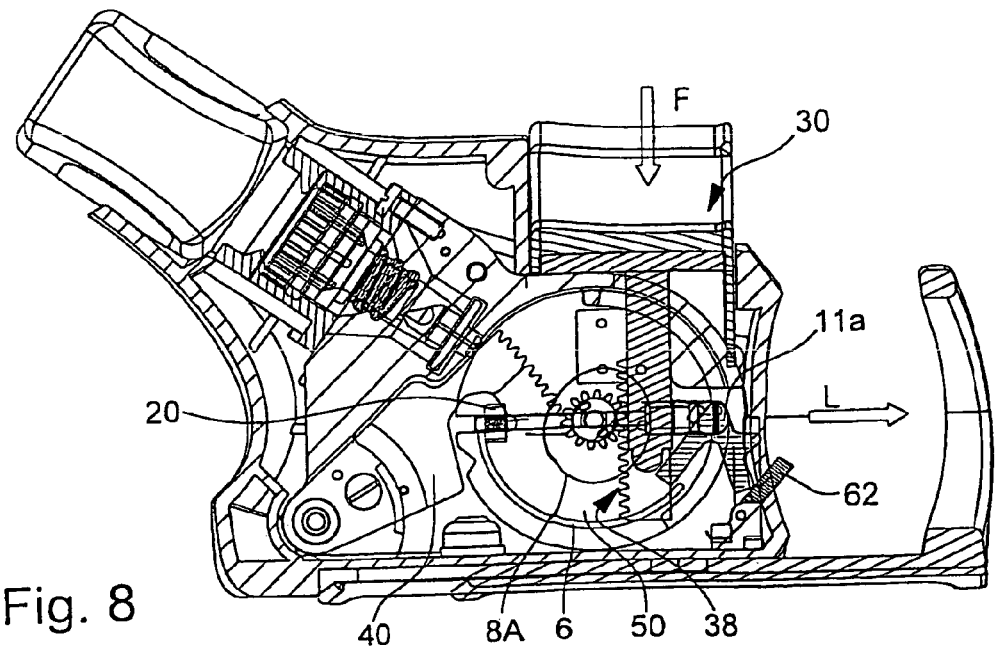
FIG. 8 corresponds to the liquid ejection phase.
Figure 8A:
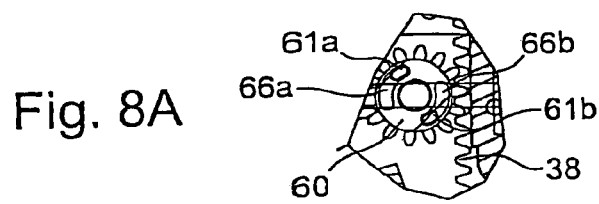
FIG. 8A shows an enlarged diagram of the pinion and rack shown in the liquid ejection of FIG. 8.

The Ejection Position (FIGS. 8 and 8A)

By exerting an additional pressure, the lateral arms of staple 20 go beyond the end of cam 6 so that the staple is no longer held. Return spring 14 of plunger 10 then pushes the plunger head to the end of dosing chamber 11 to eject the liquid. In this phase it will be observed that the pressure with which the liquid is ejected depends solely upon the characteristics chosen for spring 14, and in no way upon those of return spring 46, nor the manner in which the user exerts force F.

It will also be observed that, if the user does not reach this ejection position by releasing pressure F during filling or rotation of the drum, the dosing chamber is returned to its initial position and the unused product is re-injected into the receptacle. This constitutes a certain advantage when the product is a medicinal one whose price is generally high.

Figure 9:
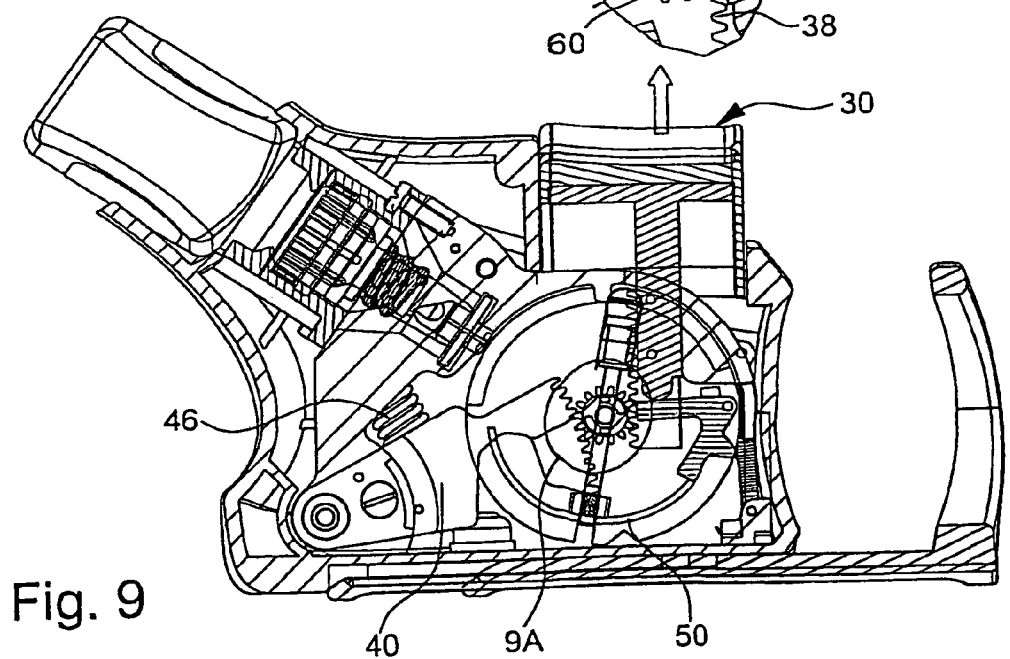
FIG. 9 shows a position of the drum during the return to its rest position.
Figure 9A:
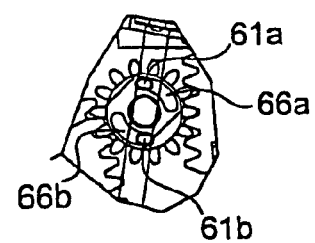

Return to the Rest Position (FIGS. 9 and 9A)

By releasing the pressure after ejecting the liquid, return spring 46 tips rack 40 in the opposite direction driving drum 50 via pinion 60 whose pins 61, 61b are stopped at the other end of holes 66a, 66b. At the end of rotation, drum 50 again occupies the position shown in FIG. 5. The apparatus is again in position for a new use.

With reference now to FIGS. 10 to 18, a second embodiment will be described hereinafter, in which the mobile element is formed by a valve 51, able to be moved by the action of the actuator, along the same direction as the latter, to place, in a first phase, the receptacle containing the liquid in communication with the dosing chamber, then, in the second phase, in communication with the exterior.

The side view of FIG. 10 shows a dispensing apparatus with the same external appearance as the previously described apparatus, and wherein the entire mechanism is masked by external cover 1, leaving only actuator 30 visible, itself including an external cover 30a, bottle 4 forming the receptacle containing a liquid, for example an ophthalmic solution, and slide 8 with its eyepiece 8a.

The actual mechanism will now be described, referring essentially to FIGS. 11 and 12. It can be seen that the mechanism is assembled by means of frame 3 for receiving a unit 9 in which the dosing chamber is formed, more clearly visible in FIG. 13A. Actuator 30 includes, perpendicular to its head 32, a plate 31 provided with an aperture 31a, and perpendicular to said plate a thick rib 33 including a snap-fitting groove 33a for a tipping element 41, having a reverse L shape, an enlarged perspective of which is shown in FIG. 12A. L-shaped element 41 forms the control member which acts, in a first movement phase of actuator 30, on means for actuating plunger 10 against the action of a return spring 14, and in a second phase on a valve 51 able to move in the same direction as actuator 30, against the action of return springs 53a, 53b disposed between said valve 51 and frame 3. As can be seen more clearly in enlarged FIG. 12A, L-shaped tipping element 41 includes a recess 41a, for receiving one end of a helical spring 47 and the other end of which is held abutting against thick rib 33 by means of a spacer 47a.

Spring 47 is intended to hold element 41 abutting against a face of plate 31 during the active phase of actuator 30, then to be compressed during the return to the rest phase to allow said element 41 to tip and move aside behind the control member of plunger 10. The junction between the small branch 43 and large branch 45 includes on each of its edges pivots 45a allowing rib 33 to snap fit into groove 33a. Large branch 45 includes, in its substantially median part, an aperture 45b opposite aperture 31a of plate 31. At its base, branch 45 includes a corner shape 35 defining on the exterior an inclined plane 35a and in the interior two inclined ramps 35b parallel to inclined plane 35a and the width of which is substantially the same as the length of pivots 45a.

Figure 12:
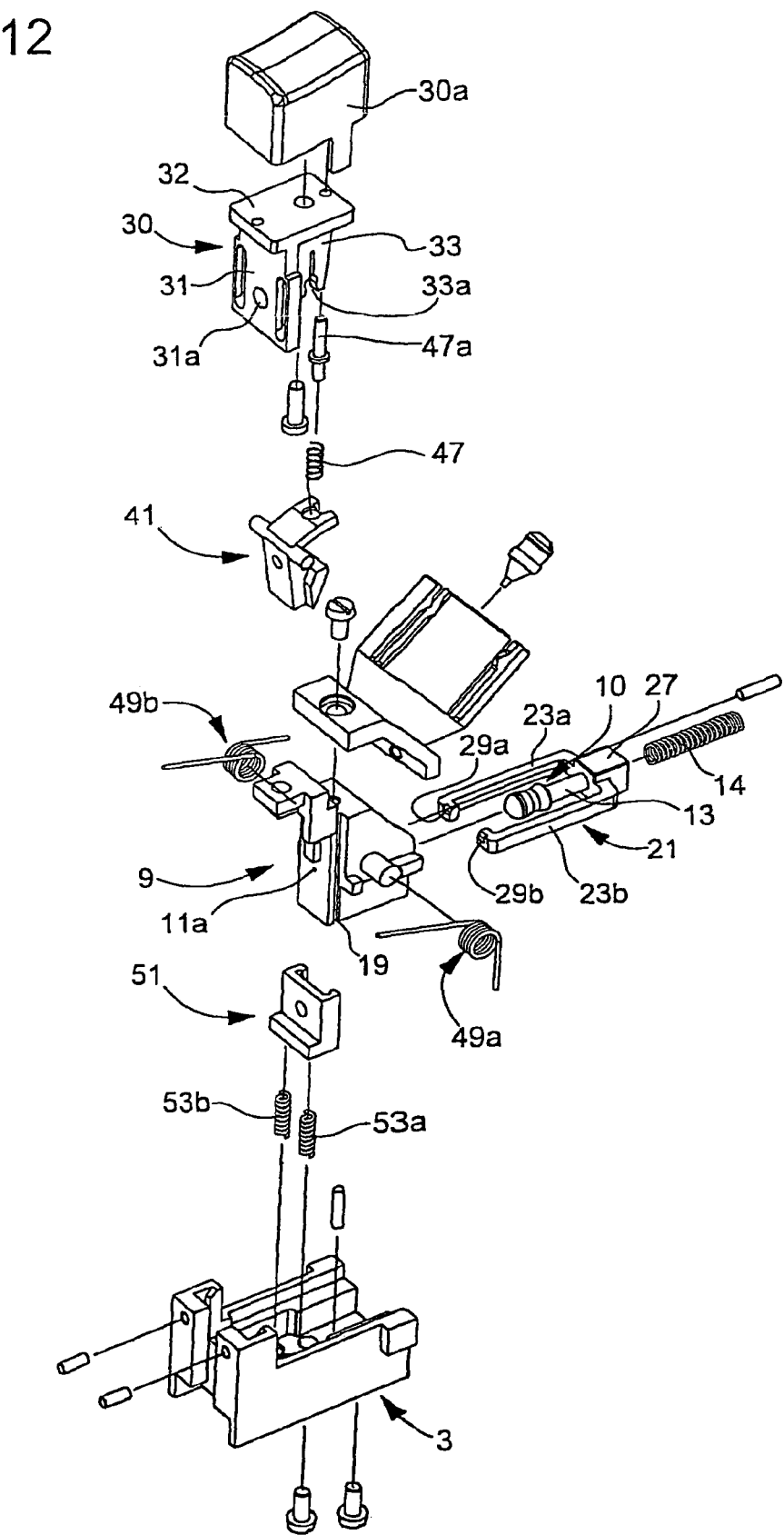
FIG. 12 is an exploded perspective view of the apparatus shown in FIG. 10.
Figure 12A:
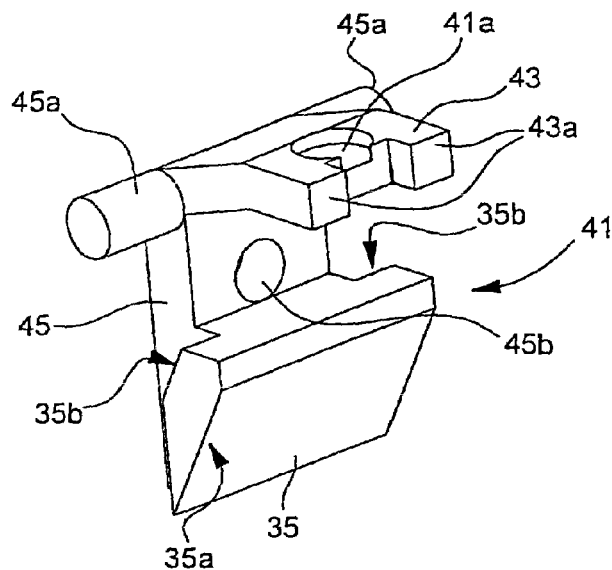
FIGS. 12A and 12C are enlarged diagrams of two elements of the mechanism from another angle.

Valve 51, which can move in sliding channels 19 of unit 9 is described in more detail with reference to enlarged FIGS. 12C and 13A. It is formed of a parallelepiped body including two edges 51a in which two grooves 51b are formed, allowing sliding on slide ways 19 of unit 9. Its base includes an edge which includes small circular recesses 55a, 55b directed downwards to position return springs 53a, 53b.

The surface delimited by the two edges 51a and pressed against the surface opposite unit 9, includes at its centre an aperture 57 and a channel 59 whose ends 59a, 59b are located on either side of aperture 57 in the plane of symmetry of valve 51. Aperture 57 is surrounded by an inner O ring joint 69a and channel 59 by an outer O ring joint 69b, these joints 69a, 69b assuring sealing during movement of the valve. The longitudinal cross-section of FIG. 13A shows the filling position in which nozzle 4a of receptacle 4 is placed in communication with orifice 11a of dosing chamber 11, by ends 59a, 59b of channel 59, which preferably has the shape of the arc of a circle. FIG. 14A shows the ejection position in which aperture 57 of the valve is brought opposite orifice 11a of dosing chamber 11, nozzle 4a then be blocked by the surface of valve 51.

Figure 12B:
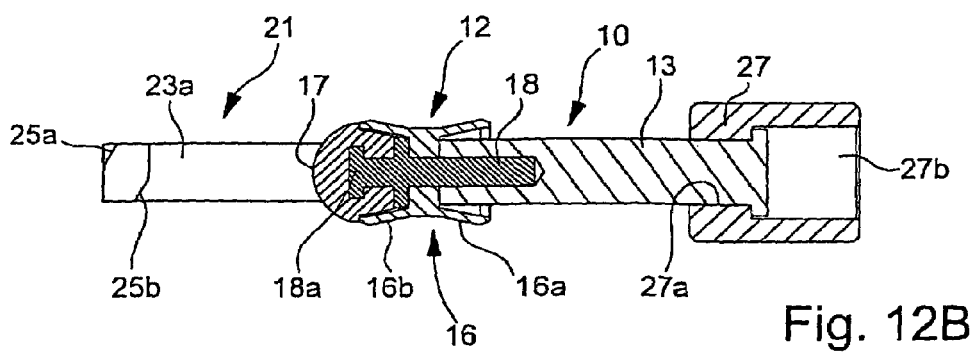
FIG. 12B is a cross-section of another element of the mechanism.
Figure 12C:
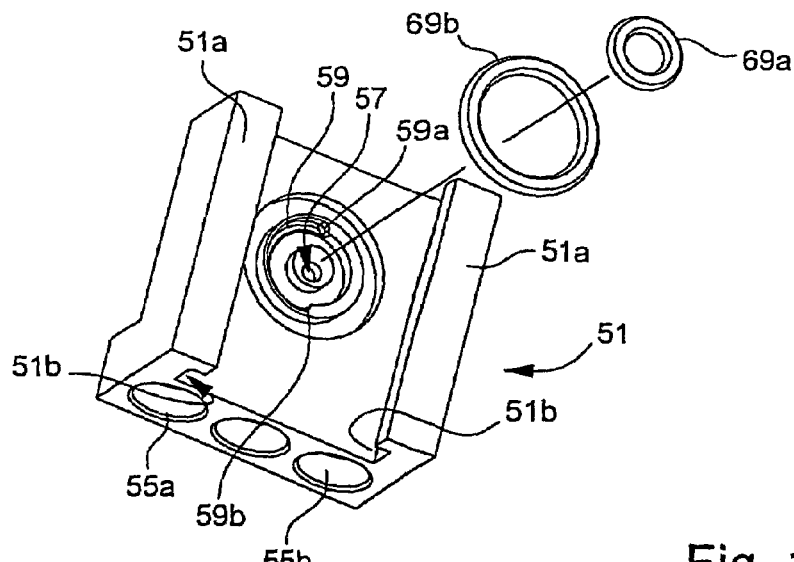

The actuating means for plunger 10, shown in cross-section in FIG. 12B is formed by a clamp 21 including two large arms 23a, 23b ending in two lugs 29a, 29b the spacing of which substantially corresponds to the width of unit 9. The large arms 23a, 23b are connected by a base 27 including a hole 27a for securing rod 13 of plunger 10 and a recess 27b for positioning return spring 14. Lugs 29a, 29b each include two chamfers 25a, 25b having substantially the same inclination as inclined planes 35a, 35b of L-shaped tipping element 41. As will be explained hereinafter for the operation of the device, chamfers 25a, 25b each co-operate with inclined planes 35a, 35b, in a first phase, to act on plunger 10 filling dosing chamber 11 and, in the second phase, to allow the device to return to the rest position.

The cross-section of FIG. 12B also shows a new design of plunger head 12 providing both greater precision in the suction/ejection of a determined quantity of liquid, and safety as regards contaminating elements able to come from the exterior through the sliding cylinder of the plunger. Plunger head 12 is formed of two parts 16, 17 assembled by an assembling member 18 having the form of a rod provided with a head 18a and a collar. The first part 16 has the shape of an inverted double cone 16a, 16b through which assembling member 18 passes, to secure it in rod 13, on the side of cone 16a. This first part 16 is made of a hard plastic material, such as polypropylene (OP) or polyethylene (PE). The second part 17 is formed by a sealing gasket 17, made of a flexible plastic material, such as a thermoplastic elastomer (TPE) or silicon, disposed in the second inverted cone 16b to fit into head 18a of pin 18. The external part of gasket 17 has a hemispheric shape substantially corresponding to the shape of the bottom wall of the dosing chamber, as can be seen in FIGS. 13A and 14A. This design allows no ullage to be left during ejection of the liquid, and thus a precise quantity of liquid to be ejected, which is particularly important for medicinal products, and particularly ophthalmic solutions. The lips (not referenced) of inverted double cones 16a, 16b enable external polluting agents to be confined at the depression of their junction.

Plunger 10 which has just been described, for this second embodiment is also that found in the first embodiment described hereinbefore. It is clear that this plunger constitutes a preferred embodiment allowing the objectives of precision and sterility to be achieved for the dispensing apparatus according to the invention, but other types of plunger can be used without departing from the scope of the mechanisms which have just been described, and the operation of which is explained in more detail with reference to FIGS. 13 to 18.

Figure 13:
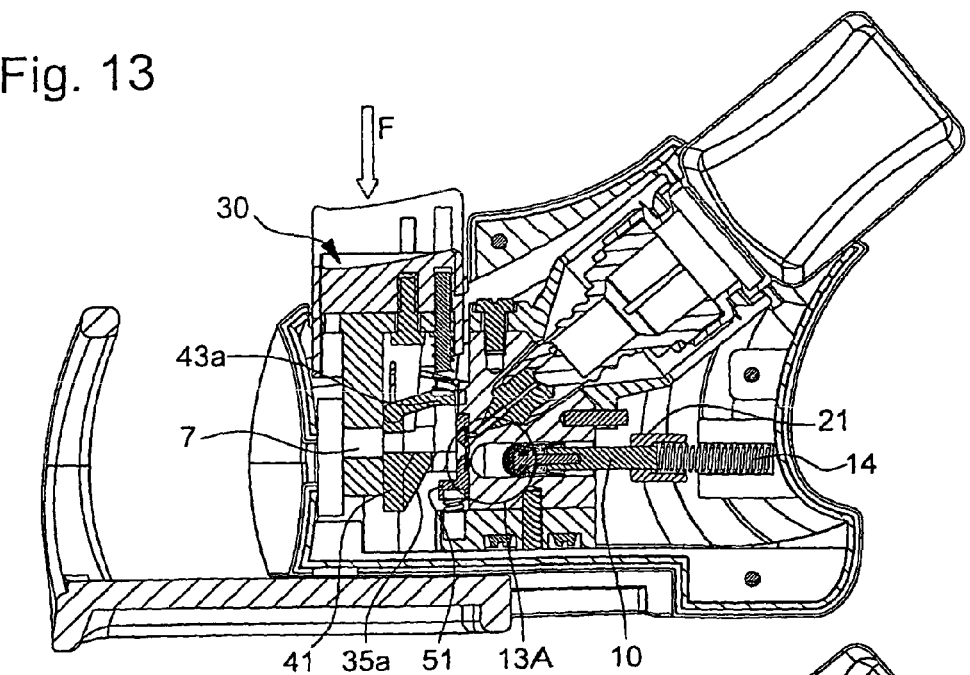
FIG. 13 corresponds to the suction phase of a determined quantity of liquid.
Figure 13A:
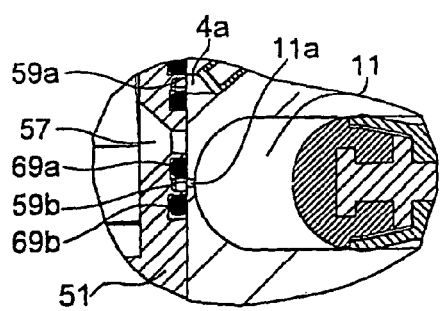
FIG. 13A is an enlarged diagram of the valve during the liquid suction phase.

Filling Position (FIGS. 13 and 13A)

Figure 11:
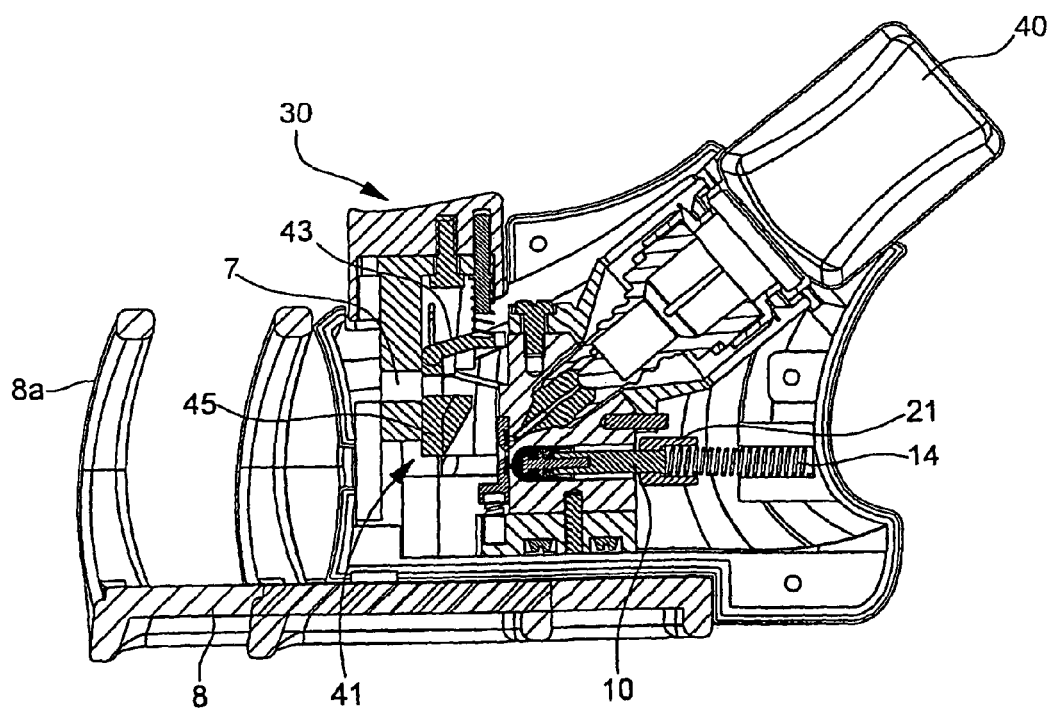
FIG. 11 is a cross-section in the plane of symmetry of the apparatus shown in FIG. 10 in the rest position.

From the rest position shown in FIG. 11, exerting a pressure F on the head of actuator 30, the inclined plane 35a of L-shaped tipping element 41 slides the corresponding chamfer 25a of clamp 21, pushing back plunger 10 and compressing spring 14. In this position the base 4a of the receptacle is in communication with the orifice of dosing chamber 11 via channel 59 and enables dosing chamber 11 to be filled.

Figure 14:
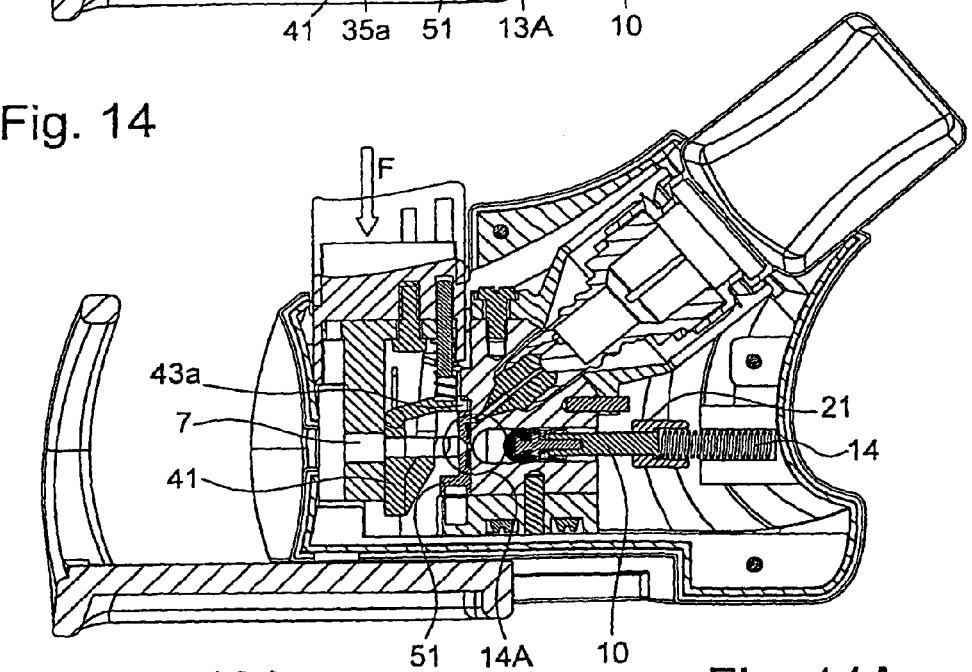
FIG. 14 shows the phase during which the valve passes into the liquid ejection phase.
Figure 14A:
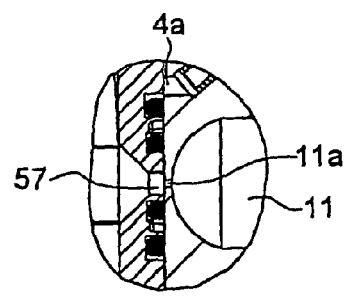
FIG. 14A is an enlarged diagram of the valve during the liquid ejection phase.

Passage into the Ejection Position
(FIGS. 14 and 14A)

By continuing to exert pressure F, the ends 43a of small arm 43 of the L-shaped tipping element press on valve 51, compressing return springs 53a, 53b to move said valve 51 to a position in which its aperture 57 is opposite orifice 11a of dosing chamber 11. In this phase, the plunger spring remains compressed.

Figure 15:
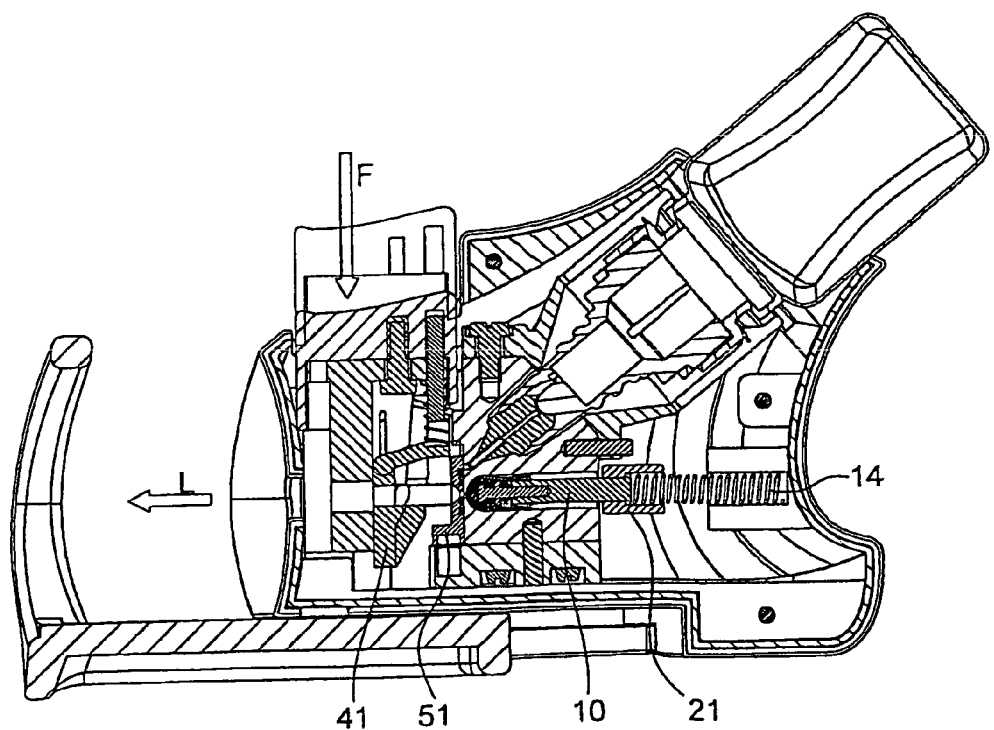
FIG. 15 shows the liquid ejection phase.

Ejection Position (FIG. 15)

By continuing to press on the actuator, L-shaped element 41 releases clamp 21, and allows the liquid to be ejected via the action of return spring 14.

As indicated in the first embodiment, if the action on the actuator is interrupted, the quantity of liquid present in the chamber is re-injected into the receptacle.

Figure 16:
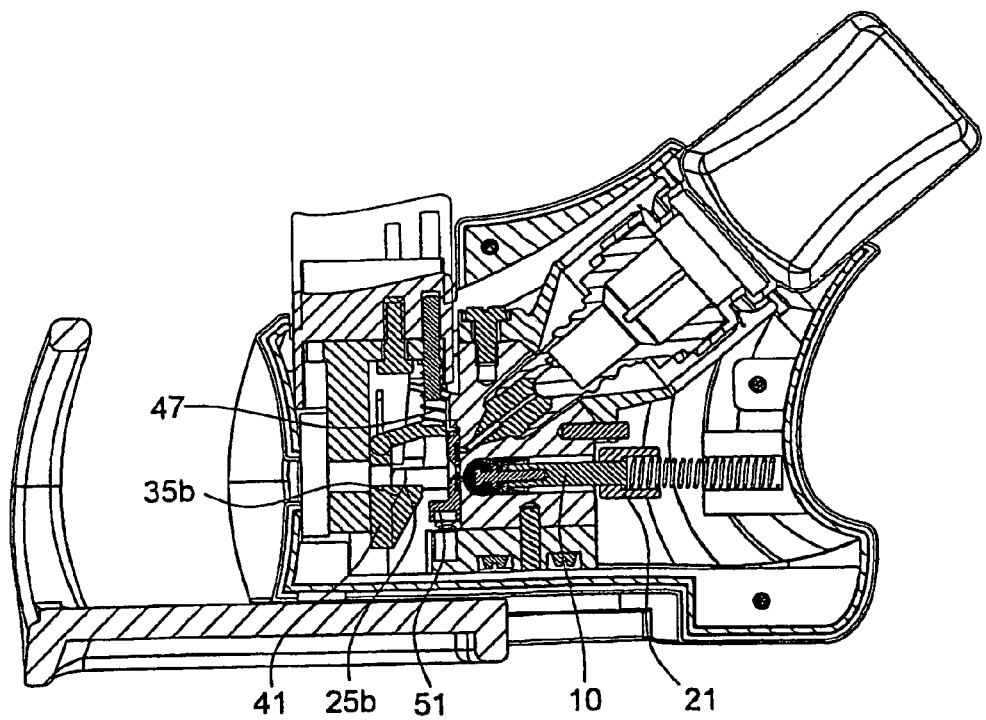
FIGS. 16, 17, 18 show the return of the apparatus to the rest position.
Figure 17:
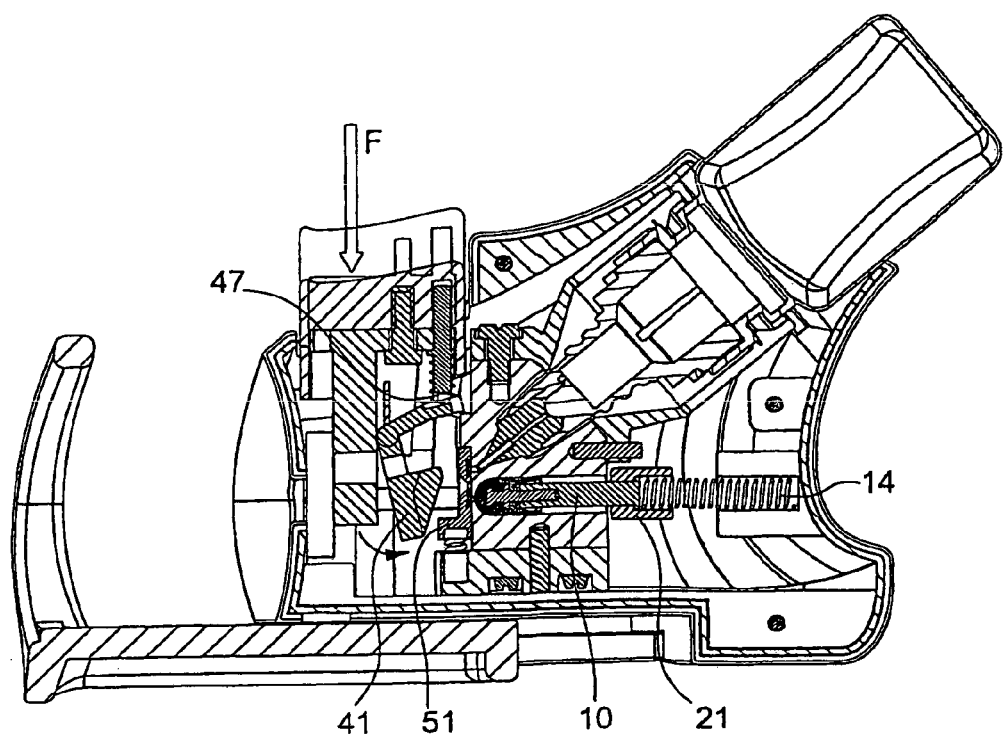
Figure 18:
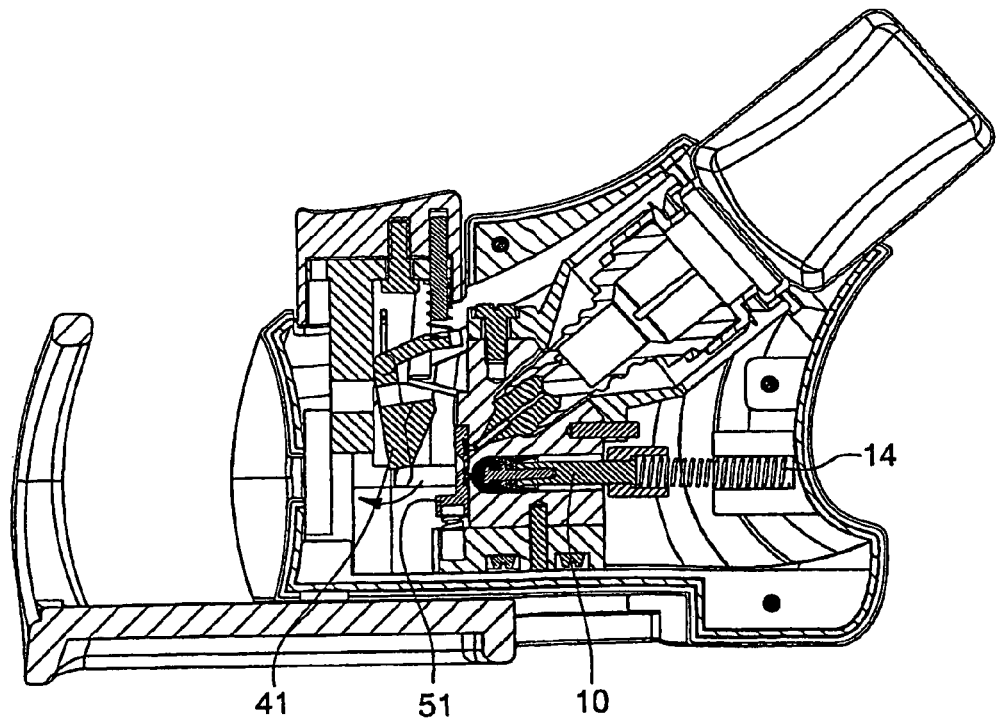

Return to the Rest Position (FIGS. 16, 17 and 18)

By releasing the pressure on the actuator, in a first phase (FIG. 16) the second inclined plane 35b of L-shaped element 41 is positioned behind the corresponding inclined plane 25b of clamp 21. In a second phase (FIG. 17), L-shaped element 41 tips compressing spring 47, and in a second phase (FIG. 18), L-shaped element 41 is returned to its initial position by spring 47. This return to the rest position is actuated by springs 49 compressed via the action of the actuator.

Figure 19:
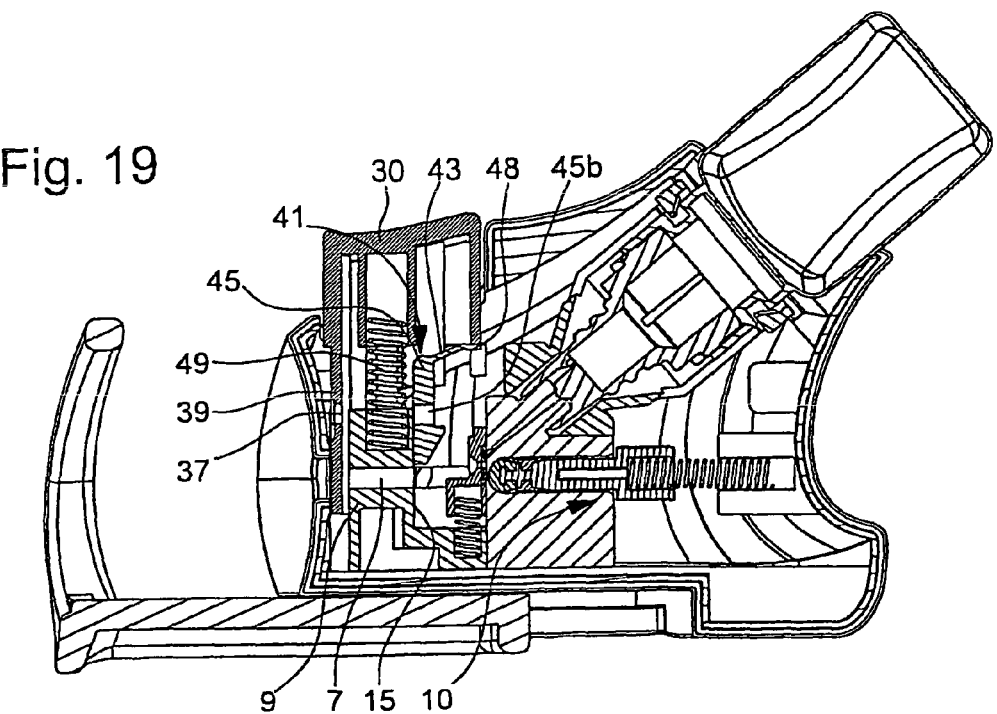
FIGS. 19, 19A and 20 respectively show in the rest position and at the end of ejection a variant illustrated with the second embodiment.
Figure 19A:
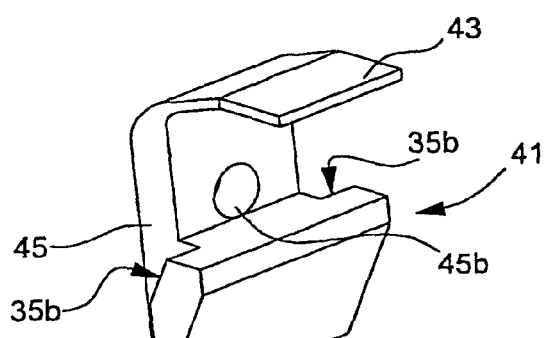
Figure 20:
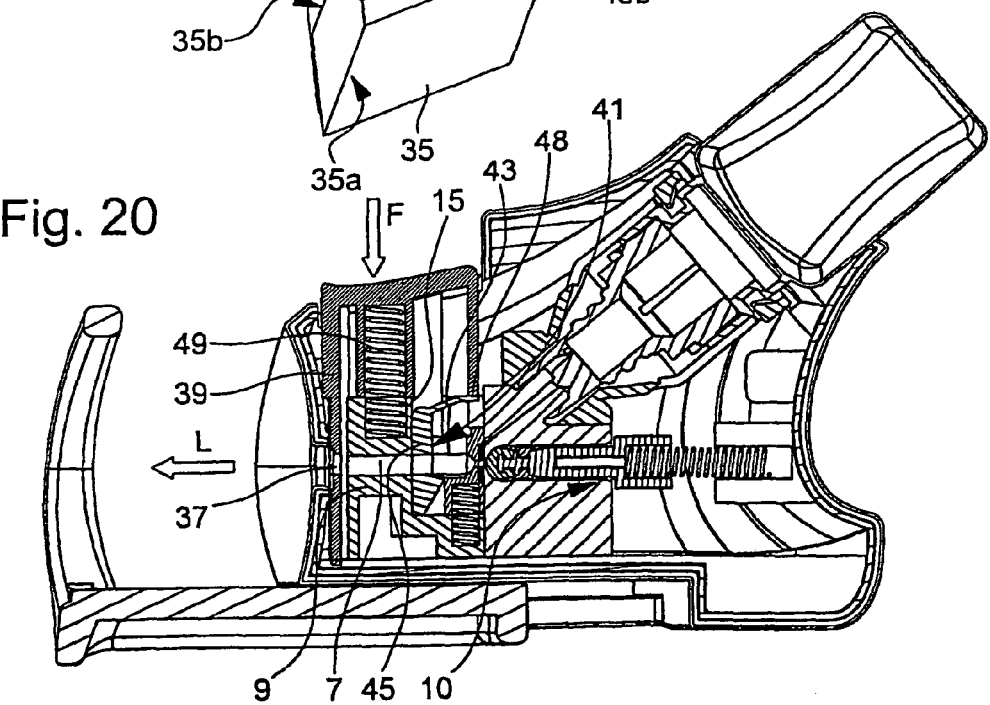

FIGS. 19, 19A and 20 show a variant of a second embodiment wherein a modified element is also applicable to the first embodiment.

In FIG. 19, which shows the apparatus in the rest position, it can be seen that actuator 30 is extended in the direction in which pressure F is exerted by a panel 39 insulating through passage 7 from the external environment when the apparatus is not being used. Panel 39 is provided with an aperture 37 which is placed opposite through passage 7 when the ejection position is reached, as shown in FIG. 20. This variant allows conditions of sterility to be increased, even if in the first embodiment the flank of the drum already forms, in the rest position, a first means for insulating the whole of the apparatus from the external environment.

FIG. 19 also shows variants relative to the second embodiment whose object is to make the apparatus according to the invention more economical.

The two actuator return springs 49a, 49b are replaced by a single spring 49 disposed between the inner face of actuator 30 and unit 9 of frame 3.

It can also be seen that the body of actuator 30, its external cover 30a and panel 39 are made in a single piece. The same is true of plunger 10 as regards clamp 21 and rod 13.

Again with reference to FIG. 19A, it can also be seen that L-shaped tipping element 41 has been modified and simplified, while fulfilling the same function, with, however, slightly different kinematics. Small branch 43 has been thinned so as to have sufficient flexibility to allow the L-shaped element to more aside upon return to the rest position; spring 47 has thus been omitted. It can also be seen that L-shaped tipping element 41 no longer includes pivots 45a, 45b. Said tipping element 41 is driven in translation by actuator 30 by having the end of its small arm 43 gripped in an extension 48 of the actuator, whereas the large arm 45, which still has a corner shaped end 35 with the two inclined planes 35a, 35b, slides over a vertical wall 15 of unit 9 when a pressure F is exerted on actuator 30.

It is clear that the devices described are arranged for multi-dose applications, i.e. applications in which doses are repeatedly drawn from a supply and repeatedly ejected. It is also clear that the devices are exemplified with features suitable for eye treatment applications. Typical parameters for this application will be given below although the invention shall not be regarded as limited to this application or any such exemplified parameter. A typical single dose volume for delivery to the eye can be less than 100 microliter, preferably less than 50 microliter, preferably less than 25 microliter, preferably less than 15 and most preferably less than 10 microliter. Generally the volume is at least 1, preferably at least 2 and most preferably at least 3 microliter. The liquid receptacle or supply line preferably has the capacity to deliver a plurality of such doses. A suitable speed for the stream of drops or jet ejected should be a balance between on one hand enough linear momentum to traverse an air gap between opening and target, without gravity assistance, and to travel fast enough not be obstructed by blinking and on the other hand not so fast as to cause inconvenient sensible impact on the eye. The ideal speed is to some extent dependent on the drop size used but as a general rule the drops should be able to traverse at least 1 cm, preferably at least 3 and most preferably at least 5 cm through air by own momentum, incorporating reasonable distances between opening and target. A suitable lower speed limit when leaving the opening is 1, m/s, preferably at least 5 m/s and most preferably at least 10 m/s. Generally the speed is lower than 200 m/s and preferably lower than 100 m/s. A suitable drop size so defined should be sufficient not to be retarded too quickly and not to be easily redirected, e.g. to be inhaled, and preferably has a minimum diameter of 20 micron, preferably not less than 50 micron and most preferably at least 100 microns. Normally the size is less than 2000 micron and preferably less than 1500 micron. The stream may take the form of a shower or spray of atomized liquid droplets but preferably the stream is narrow and fairly coherent although even such a stream tend to break up into individual droplets after a certain time of distance. The above given values are intended to relate to spherical droplets and for multiple droplets to the weight average of particle diameters. A coherent stream tends to break up into droplets of a diameter of roughly double the diameter of the stream. Accordingly suitable opening diameters for the containers are about half the above given drop diameters or roughly between 10 and 1000 microns, preferably between 20 and 800 microns. The above considerations are fairly independent of liquid viscosity and tend to apply both for solutions and ointments. It is desirable that the whole dose can be delivered in a time shorter than the blink reflex time, i.e. in a time shorter than about 150 ms, preferably shorter than 100 ms and most preferably shorter than 75 ms.

The invention claimed is:

1. Dispensing apparatus for a liquid product contained in a receptacle, comprising a feed nozzle, said apparatus including an assembly housing or a frame for receiving a mechanism actuated by exerting a pressure on an actuator to draw from the receptacle through the orifice of a dosing chamber a determined quantity of said liquid by means of a plunger compressing a return spring, and to then eject said liquid to the exterior, wherein the mechanism includes an element that is mobile in rotation or translation via the action of the actuator, said mobile element adapted to remain in a first position at the start or rest of the actuator's travel, then to act on a control member for the plunger to fill the dosing chamber with said liquid and to compress the return spring of said plunger, and, at the end of travel, to then pass into a second position placing said dosing chamber in communication with the exterior by the same orifice as that allowing the liquid to be drawn and, releasing the return spring of the plunger, to drive the liquid from the chamber through a through passage of the housing or the frame.

2. Apparatus according to claim 1, wherein the actuator is adapted to return to the rest position by resilient return means wound by the travel of said actuator.

3. Apparatus according to claim 2, including means for re-injecting the liquid contained in the dosing chamber into a receptacle before the actuator has reached the rest position if the pressure is released before the mobile element has reached the second position for election.

4. Apparatus according to claim 1, wherein the actuator further includes a panel blocking the through passage of the housing or frame in the rest position, said panel including an opening that faces said passage in the ejection position.

5. Apparatus according to claim 1, wherein the mobile element is formed by a drum provided on its flanks with studs rotatably mounted in the housing or frame, in its diametral part, an assembly formed by the dosing chamber, the plunger and the return spring, said drum being adapted to occupy a first filling position in which the orifice of the dosing chamber is facing the feed nozzle of the receptacle, and after a rotation through an angle, to occupy a second ejection position in which said orifice of the dosing chamber is facing the through passage of the housing.

6. Apparatus according to claim 5, wherein each rotation stud of the drum includes a loose pinion whose shake is limited by two pins secured to said pinion and engaged in elongated bean-shaped holes of the drum, and wherein the actuator is U shaped surrounding the drum, each arm including both a stop member and a straight rack meshing with the pinion, said stop member adapted to actuate, in a first movement phase of the actuator, a lever articulated in its median part in the housing and the end of which is adapted to move a control member for the plunger for filling the dosing chamber, and said straight rack adapted to drive, in a second movement phase of the actuator, the pinion and the drum to make it rotate through the angle.

7. Apparatus according to claim 6, further including a safety catch pivoted in the housing and engaged in a notch of the drum, adapted to immobilize said drum while the dosing chamber is being filled, said catch then being releasable from the notch by a snug of the lever to allow the drum to rotate until said drum reaches the liquid ejection position.

8. Apparatus according to claim 6, wherein the plunger control member is formed by a staple secured to the end of the plunger, compressing the return spring and including laterally two branches, the ends of which are adapted to follow, once filling is complete, the external contour of a circular cam, formed in the housing or frame, during rotation of the drum from the filling position to the ejection position in which the staple is released from the cam allowing the return spring to push the plunger.

9. Apparatus according the claim 1, wherein the resilient means of the actuator comprise two pivoting racks connected by a bridge compressed by a spring, the teeth of said pivoting racks meshing with the pinions of the drum.

10. Apparatus according to claim 1, wherein the dosing chamber is formed in a unit secured to the housing or frame, and the mobile element is formed by a valve that is movable by the actuator against the return force of springs from a first filling position by means of a passage formed in the thickness of said valve and connecting the orifice of the dosing chamber and the nozzle of the receptacle, to a second ejection position in which the orifice of the dosing chamber is placed in communication with the exterior through a hole in the valve facing the through passage of the housing or frame.

11. Apparatus according to claim 10, wherein the actuator includes, parallel to its direction of movement, a plate provided with an opening and against which a reverse L-shaped part is mounted so as to tip, the large arm of said part being provided with an opening facing the opening of the plate and including on each side of its base, a first inclined plane adapted to actuate, in a first movement phase of the actuator, the plunger control member for filling the dosing chamber, and the end of the small arm of said part adapted to act, in a second movement phase of the actuator, on the valve to bring said valve into a position where the orifice of the dosing chamber, the openings of the valve and the plate and the through passage of the housing are aligned to allow the liquid to be ejected.

12. Apparatus according to claim 11, wherein, during the first and second movement phases of the actuator, the large arm of the reverse L-shaped part is adapted to be held pressed against the plate by means of a spring arranged between the head of the actuator and the small arm of said part.

13. Apparatus according to claim 11, wherein the plunger control member comprises a clamp, the base of which is adapted to allow the plunger to be fixed the return spring to be held, and two branches, ending in two lugs, each provided two chambers substantially parallel to the inclined plane of the L-shaped tipping part, to be connected.

14. Apparatus according to claim 11, wherein the reverse L-shaped tipping part further includes on each of its edges a second inclined plane parallel to the first inclined plane adapted to allow said part to move aside by tipping against the chambers of the clamp when the actuator is returned to the rest position by the resilient return means.

15. Apparatus according to claim 14, wherein the resilient return means comprise two bending springs, one end of which is secured to the unit of the housing or frame and the other end of which abuts underneath the head of the actuator.

16. Apparatus according to claim 14, wherein the resilient return means comprise a helical spring disposed between the head of the actuator and the unit of the housing or frame.

17. Apparatus according to claim 10, wherein the unit includes vertically a wall against which a reverse L-shaped part can slide or tip, the large arm of said part being provided with an opening and the small arm being flexible and gripped at its end in an extension of the actuator, said L-shaped part including on each side of its base, a first inclined plane adapted to actuate, in a first movement phase of the actuator, the plunger control member for filing the dosing chamber, and the end of the small arm of said part adapted to act, in a second movement phase of the actuator, on the valve to bring said valve into a position where the orifice of the dosing chamber, the openings of the valve and the plate and the through passage of the housing are aligned to allow the liquid to be ejected.

18. Apparatus according to claim 1, wherein the receptacle is formed by a bottle fixed in the housing or the frame.

19. Apparatus according to claim 1, wherein the housing or the frame further includes a sliding element allowing the distance between the point of ejection of the liquid and the point of impact on a target to be adjusted.

20. Apparatus according to claim 1, wherein the liquid is an ophthalmic product and the target is a patient's eye.

21. Apparatus according to claim 1, wherein the plunger has a head formed by a reversed double cone made of a rigid material, one end of which is fixed onto the rod of the plunger, and the other end of which, forming the plunger head, is fitted with a flexible material with a rounded end.

22. Apparatus according to claim 21, wherein the bottom of the dosing chamber has a complementary shape to the end of the plunger head.

23. Apparatus according to claim 1, wherein the same actuator is adapted to be used for the actions from the rest position to ejection.

24. Apparatus according to claim 1, wherein the actuator is adapted to perform a substantially continuous movement.

25. A dispensing apparatus for a liquid product, the apparatus comprising a) a housing or frame, b) a receptacle for the liquid with a feed nozzle arranged substantially stationary with respect to the housing or frame, c) a dosing chamber having an orifice, d) a mechanism arranged to allow at least ejection of said liquid through the orifice, and e) a through passage arranged to allow the at least ejection of said liquid to pass in a direction different from the feed nozzle or opening, wherein i) the mechanism comprises a mobile element movable with respect to the housing or frame between at least a first position in which the orifice of the dosing chamber and the feed nozzle or opening are in flow communication and a second position in which the orifice and the through passage are in flow communication, and ii) the mechanism is arranged to allow aspiration of said liquid through the orifice when the mobile element is in the first position and ejection of said liquid through the orifice when the mobile element is in the second position.

26. The apparatus of claim 25, wherein the mobile element is adapted to move or carry the dosing chamber between a filling position, when the mobile element is in the first position, and an ejection position, when the mobile element is in the second position.

27. The apparatus of claim 26, wherein the dosing chamber comprises a substantially cylindrical barrel, defining a concentric barrel axis.

28. The apparatus of claim 27, wherein the mobile element is adapted to move or carry the dosing chamber in a rotational movement around a rotation axis different from the barrel axis.

29. The apparatus of claim 28, wherein the rotation axis is substantially perpendicular to the barrel axis.

30. The apparatus of claim 25, wherein the mobile element comprises a valve, having a passage and a hole or the through passage, the passage being adapted to connect the nozzle or opening with the orifice when the mobile element is in the first position and to align the orifice with the hole or the through passage when the mobile element is in the second position.

31. The apparatus of claim 30, wherein the passage is adapted to be shut off when the mobile element is in the second position.

32. The apparatus of claim 31, wherein the passage is shut off in both ends.

33. The apparatus of claim 30, wherein the dosing chamber is arranged substantially fixed with respect to the housing or frame.

34. The apparatus of claim 25, wherein the mechanism is adapted to perform in sequence the aspiration of liquid in the first position, the movement of the mobile element to the second position, and the ejection of liquid in the second position.

35. The apparatus of claim 34, wherein the mechanism is adapted to perform the aspiration by retraction of a pump member against a return spring and to perform the ejection by release of the return spring.

36. The apparatus of claim 34, wherein the mechanism is adapted to return to the start or rest position after liquid ejection.

37. The apparatus of claim 36, wherein the mechanism is adapted to return to the start or rest position also before liquid ejection.

38. The apparatus of claim 37, wherein the mechanism is adapted to reinject the aspirated liquid in the receptacle if the return takes place before ejection.

39. The apparatus of claim 36, wherein a return member is arranged to bias the mechanism towards the start or rest position.

40. The apparatus of claim 25, wherein at least one actuator is included and is adapted to operate the mechanism.

41. The apparatus of claim 40, wherein the actuator is arranged to be maneuvered by application of manual force.

42. The apparatus of claim 40, wherein the actuator is adapted to perform a substantially continuous movement during which the mechanism performs at least the aspiration step and the movement of the mobile element between the first position and the second position.

43. The apparatus of claim 42, wherein the substantially continuous movement also includes the ejection step for the mechanism.

44. The apparatus of claim 43, wherein the actuator is adapted to give a tactile feed-back immediately before the ejection step in the continuous movement.

45. The apparatus of claim 26, wherein the dosing chamber comprises a substantially cyclindrical barrel, defining a concentric barrel axis and having a substantially constant cross-section area perpendicular to the barrel axis, and a plunger inserted in the barrel and being movable along the barrel axis.

46. The apparatus of claim 45, wherein the orifice has a substantially smaller cross-section area than the barrel.

47. The apparatus of claim 46, wherein the length of the orifice in the liquid flow direction is substantially shorter than the plunger movement during aspiration and/or ejection.

48. The apparatus of claim 47, wherein the orifice length to plunger movement length is less than 1:5.

49. The apparatus of claim 25, wherein the orifice, is adapted to create a liquid spray.

50. The apparatus of claim 25, wherein the orifice is adapted to create a substantially coherent stream.

51. The apparatus of claim 25, wherein, in the second position, the orifice is adapted to eject liquid substantially directly into the air.

52. The apparatus of claim 51, wherein the through passage is substantially wider than the width of the orifice.

53. The apparatus of claim 52, wherein any apparatus part in front of the orifice is substantially wider than the orifice.

54. The apparatus of claim 25, comprising an eye piece or eye cup adapted to define a predetermined distance to the orifice.

55. The apparatus of claim 47, wherein the orifice length to plunger movement length is less that 1:10.

56. The apparatus of claim 47, wherein the orifice length to plunger movement length is less than 1:20.

* * * * *